(12) United States Patent
Shinohara et al.

(10) Patent No.: US 9,545,627 B2
(45) Date of Patent: Jan. 17, 2017

(54) PROTEIN ADSORBENT

(71) Applicant: ASAHI KASEI CHEMICALS CORPORATION, Tokyo (JP)

(72) Inventors: Naoyuki Shinohara, Tokyo (JP); Yuta Sato, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 14 days.

(21) Appl. No.: 14/363,919

(22) PCT Filed: Dec. 12, 2012

(86) PCT No.: PCT/JP2012/082216
§ 371 (c)(1),
(2) Date: Jun. 9, 2014

(87) PCT Pub. No.: WO2013/089141
PCT Pub. Date: Jun. 20, 2013

(65) Prior Publication Data
US 2014/0357742 A1   Dec. 4, 2014

(30) Foreign Application Priority Data

Dec. 15, 2011 (JP) ................................. 2011-274619

(51) Int. Cl.
*B01J 41/20* (2006.01)
*B01J 39/04* (2006.01)
(Continued)

(52) U.S. Cl.
CPC ............. *B01J 41/20* (2013.01); *B01J 20/3078* (2013.01); *B01J 20/327* (2013.01);
(Continued)

(58) Field of Classification Search
USPC ............................................. 521/32; 530/415
See application file for complete search history.

(56) References Cited

U.S. PATENT DOCUMENTS 5,547,575 A   8/1996  Demmer et al.
6,780,327 B1  8/2004  Wu et al.
(Continued)

FOREIGN PATENT DOCUMENTS

EP   2 226 331        9/2010
EP   2226331 A1 *    9/2010
(Continued)

OTHER PUBLICATIONS

International preliminary report on patentability issued for Application No. PCT/JP2012/082216, mail date is Jun. 26, 2014.
(Continued)

*Primary Examiner* — Peter D Mulcahy
*Assistant Examiner* — Henry Hu
(74) *Attorney, Agent, or Firm* — Greenblum & Bernstein, P.L.C.

(57) ABSTRACT

A method for producing a protein adsorbent comprising a substrate and a molecular chain fixed on the surface of the substrate is disclosed. The method comprises, in this order: a dry-heat treatment step of heating a pretreatment adsorbent comprising the substrate and the molecular chain fixed on the surface of the substrate, in which the molecular chain contains a weak electrolytic ion-exchange group; and a wet-heat treatment step of heating the pretreatment adsorbent in a moistened state with a liquid or steam to obtain the protein adsorbent.

5 Claims, 1 Drawing Sheet

(51) Int. Cl.
  *B01J 39/20* (2006.01)
  *B01J 39/26* (2006.01)
  *B01J 41/04* (2006.01)
  *B01J 41/12* (2006.01)
  *B01J 41/14* (2006.01)
  *B01J 47/12* (2006.01)
  *B01J 20/30* (2006.01)
  *B01J 20/32* (2006.01)
  *C07K 1/22* (2006.01)

(52) U.S. Cl.
  CPC ......... *B01J 20/3278* (2013.01); *B01J 39/046* (2013.01); *B01J 39/20* (2013.01); *B01J 39/26* (2013.01); *B01J 41/046* (2013.01); *B01J 41/125* (2013.01); *B01J 41/14* (2013.01); *B01J 47/12* (2013.01); *B01J 47/123* (2013.01); *C07K 1/22* (2013.01)

(56) References Cited

U.S. PATENT DOCUMENTS

| | | | |
|---|---|---|---|
| 2010/0228010 A1* | 9/2010 | Shirataki | B01D 69/08 530/413 |
| 2010/0248954 A1 | 9/2010 | Furumoto et al. | |
| 2014/0235837 A1* | 8/2014 | Sato | C07K 1/22 530/415 |

FOREIGN PATENT DOCUMENTS

| | | | |
|---|---|---|---|
| EP | 2 762 486 | | 8/2014 |
| EP | 2762486 A1 | * | 8/2014 |
| JP | 5-064748 | | 3/1993 |
| JP | 09-127082 | * | 5/1997 |
| JP | 09-127082 A | | 5/1997 |
| JP | 2006-519273 | | 8/2006 |
| JP | 2008/501808 | | 1/2008 |
| JP | 2008-045906 | * | 2/2008 |
| JP | 2009-053191 | | 3/2009 |
| TW | 2009-36238 | * | 9/2009 |
| TW | 200936238 | * | 9/2009 |
| TW | 200936238 A | | 9/2009 |
| WO | 2009/054226 | | 4/2009 |
| WO | WO-2009/054226 A1 | * | 4/2009 |
| WO | 2010-141426 A1 | | 12/2010 |
| WO | WO-2010/141426 A1 | * | 12/2010 |
| WO | WO-2013/089141 A1 | * | 6/2013 |

OTHER PUBLICATIONS

European Search Report for European Patent Application No. 12858220.2, mailed Jul. 17, 2015.
International Search Report for PCT/JP2012/082216, mailed Mar. 12, 2013.
Saito et al., Charged Polymer Brush Grafted Onto Porous Hollow-Fiber Membrane Improves Separation and Reaction in Biotechnology, *Separation Science and Technology* 37(3):535-554, 2002.

* cited by examiner

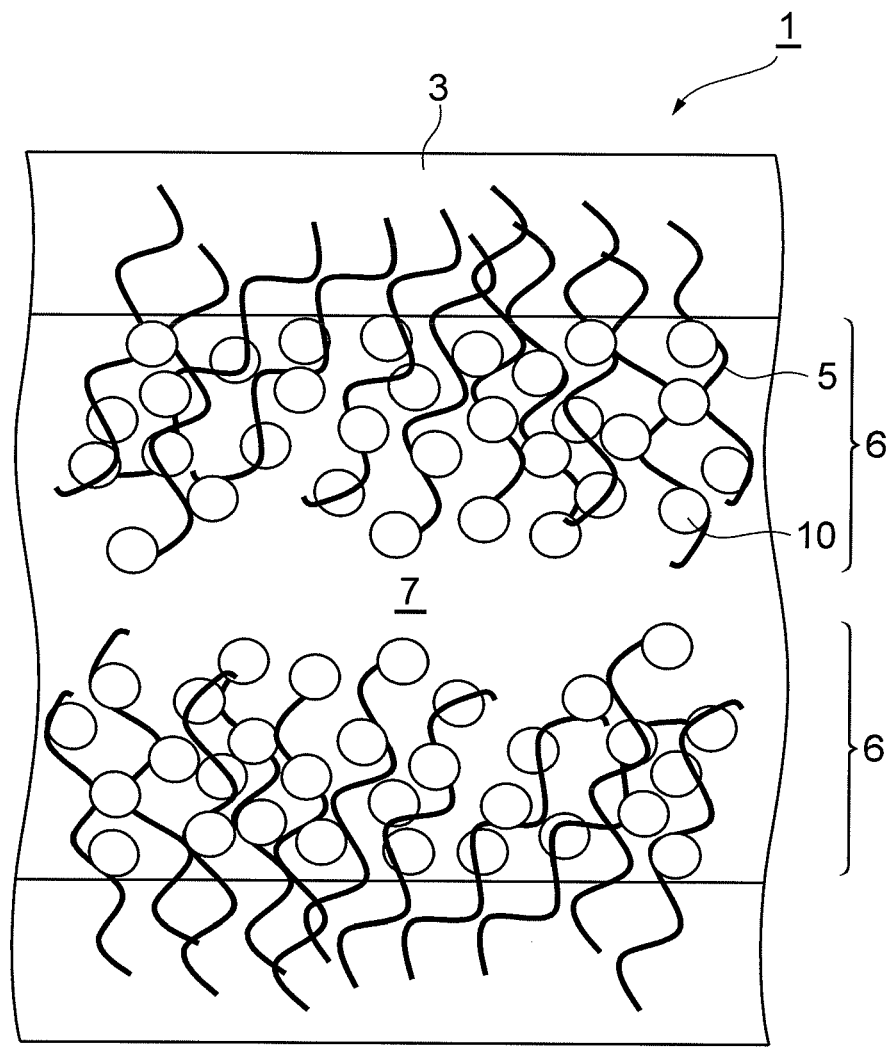

PROTEIN ADSORBENT

TECHNICAL FIELD

The present invention relates to a protein adsorbent. Moreover, the present invention relates to a column and a module comprising a protein adsorbent.

BACKGROUND ART

Technologies relating to a protein adsorbent for large-scale purification of a protein are disclosed in, for example, Patent Literature 1 to 5.

Patent Literature 1 discloses a purification method of a protein, which comprises a filtering step using a porous membrane having a graft chain on a pore surface, in which an anion-exchange group is fixed to the graft chain.

Patent Literature 2 discloses a porous adsorption medium in which a porous substrate is covered with an adsorption material having a cross-linked polymer to which a primary amine group is bonded.

Patent Literature 3 discloses a composite material comprising: a support structural member in which a plurality of holes extends; and macroporous cross-linked gel arranged in the holes of the support structural member and filling the holes of the support structural member, and states that it is suitable for use in separation of substances by adsorption.

Patent Literature 4 provides a positively-charged porous membrane composed of: a cross-linked coating film having a cation functional group; and a porous substrate, and states that it can be used for filtration and purification of biomolecules such as proteins, nucleic acids, and endotoxins.

Patent Literature 5 discloses an adsorption body capable of performing high-speed adsorptive purification of a protein or the like, in which a functional group having protein adsorption ability is fixed on the surface of polymer substrate particles through a polymer chain, and a producing method thereof.

An example in which surface modification of a substrate was performed by a coating film into which an amino group or a sulfonate group generally known as a functional group that can interact with a protein is introduced is disclosed in Patent Literature 6. Patent Literature 6 discloses a method in which graft polymerization is performed on the substrate by forming a coating film of an N-halogenated compound (polymer or polymer precursor) on the surface of a polymer porous substrate film and bringing a graft initiator into contact with a monomer. Furthermore, a film obtained by graft polymerization of glycidyl methacrylate (GMA) as the monomer, and subsequent introduction of a tertiary amino group/quaternary ammonium group into the epoxy group of GMA by a secondary/tertiary amine or sulfonation of the epoxy group by treatment with a sulfonate ion is described.

CITATION LIST

Patent Literature

Patent Literature 1: International Publication No. WO 2009/054226
Patent Literature 2: Japanese Patent Laid-Open No. 2009-53191
Patent Literature 3: National Publication of International Patent Application No. 2006-519273
Patent Literature 4: U.S. Pat. No. 6,780,327
Patent Literature 5: Japanese Patent Laid-Open No. 2008-45906
Patent Literature 6: U.S. Pat. No. 5,547,575

Non Patent Literature

Non Patent Literature 1: Kyoichi Saito, CHARGED POLYPER BRUSH GRAFTED ONTO POROUS HOLLOW-FIBER MEMBRANE IMPROVES SEPARATION AND REACTION IN BIOTECNOLOGY, Separation Science and Technology, ENGLAND, Taylar & Francis, 2002, 37(3), 535-554

SUMMARY OF INVENTION

Technical Problem

An adsorbent in which a molecular chain having a functional group having protein adsorption ability is fixed to a surface of a polymer molded body or its coating film, which is disclosed in, for example, Patent Literature 1, 5 and 6, is expected to achieve a certain high level in adsorption performance and a purifying treatment speed.

However, after studying the adsorbent having such a structure in detail, it was made clear that variation in adsorption performance tends to be large and this can become a significant problem in putting the adsorbent into practical use. Specifically, a difference of the adsorption performance between immediately after production and after storing for a long time tends to be large. Therefore, there were problems that it is difficult to predict the timing of adsorption breakthrough, for example, it is difficult to design purification equipment using a number of adsorbents and to design operating conditions, and furthermore, quality loss of a purified liquid tends to occur by occurrence of leakage of a constituent that should be removed through adsorption.

Accordingly, it is a main object of the present invention to improve stability of adsorption performance of a protein adsorbent having a molecular chain containing a weak electrolytic ion-exchange group having protein adsorption ability and fixed on the surface of a substrate including a polymer molded body.

Solution to Problem

The present inventors made extensive research so as to solve the above-described subject, and found that using a change ratio of an adsorption capacity when performing test treatment of an adsorbent under specific moistened conditions as an index is effective for achieving the above-described object to complete the present invention based on such knowledge.

That is, the present invention relates to the following.

[1]

A method for producing a protein adsorbent comprising a substrate and a molecular chain fixed to a surface of the substrate, the method comprising, in this order:

a dry-heat treatment step of heating a pretreatment adsorbent comprising the substrate and the molecular chain fixed on the surface of the substrate, the molecular chain containing a weak electrolytic ion-exchange group; and a wet-heat treatment step of heating the pretreatment adsorbent in a moistened state with a liquid or steam to obtain the protein adsorbent.

[2]

The method according to [1], further comprising a molecular chain forming step of fixing the molecular chain on the surface of the substrate before the dry-heat treatment step.

[3]

The method according to [1] or [2], wherein a dynamic adsorption capacity of bovine serum albumin or lysozyme of the protein adsorbent is 5 mg/mL or more.

[4]
The method according to any one of [1] to [3], wherein the dry-heat treatment step comprises heating the pretreatment adsorbent at 40° C. to 130° C. for 1 hour or more.

[5]
The method according to any one of [1] to [4], wherein the wet-heat treatment step comprises heating the pretreatment adsorbent at 40 to 120° C. for 30 minutes or more in the moistened state with a liquid or steam.

[6]
The method according to any one of [1] to [5], wherein the moistened state of the protein adsorbent is maintained after the wet-heat treatment step.

[7]
A protein adsorbent comprising a substrate and a molecular chain fixed to a surface of the substrate, the molecular chain containing a weak electrolytic ion-exchange group, wherein
when test treatment in which the protein adsorbent moistened with a 20 mM tris-hydrochloric acid buffer solution containing 1 mol/L sodium chloride is heated at 50° C. for 8 hours is performed, a change ratio of a dynamic adsorption capacity of the protein adsorbent before and after the test treatment is within ±5%.

[8]
The protein adsorbent according to [7], wherein the molecular chain is covalently-bonded to a compound constituting the substrate.

[9]
The protein adsorbent according to [7] or [8], wherein the substrate is a porous body.

[10]
The protein adsorbent according to any one of [7] to [9], wherein the substrate is hollow fibrous.

[11]
The protein adsorbent according to any one of [7] to [10], wherein the weak electrolytic ion-exchange group is a tertiary amino group.

[12]
The protein adsorbent according to any one of [7] to [11], wherein the molecular chain is a linear polymer chain formed by graft polymerization.

[13]
A module comprising the protein adsorbent according to any one of [7] to [12].

[14]
A column comprising the protein adsorbent according to any one of [7] to [12].

Advantageous Effects of Invention

According to the present invention, stability of adsorption performance of a protein adsorbent comprising a molecular chain containing a weak electrolytic ion-exchange group having protein adsorption ability and fixed on the surface of a substrate comprising a polymer molded body can be improved. Since the adsorption performance is stable, even when constituting a large-size purification device using the adsorbent, design of purification equipment and design of operating conditions are easy, and risk of quality loss of a purified liquid is small.

BRIEF DESCRIPTION OF DRAWINGS

FIG. 1 is a schematic diagram showing one embodiment of a protein adsorbent.

DESCRIPTION OF EMBODIMENTS

Hereinafter, a preferred embodiment of the present invention will be described in detail. However, the present invention is not limited to the following embodiment and may be embodied in various ways within the gist of the present invention.

FIG. 1 is a schematic diagram showing one embodiment of a protein adsorbent. An adsorbent 1 shown in FIG. 1 comprises a substrate 3 comprising a polymer molded body containing a polymer compound, and a molecular chain 5 fixed on the surface of the substrate 3. The molecular chain 5 contains a weak electrolytic ion-exchange group having protein adsorption ability. The molecular chain 5 forms an adsorption layer 6. One example of the polymer molded body according to the present embodiment is a porous body forming a pore 7, and when a solution containing a protein passes through the pore 7, a protein 10 is adsorbed by the adsorbent 1 mainly due to the action of the weak electrolytic ion-exchange group.

When test treatment in which the adsorbent 1 that is moistened with a 20 mM tris-hydrochloric acid buffer solution containing 1 mol/L sodium chloride (hereinafter, sometimes referred to as "salt buffer") is heated at 50° C. for 8 hours is performed, the change ratio of the dynamic adsorption capacity of the adsorbent 1 before and after the test treatment is small. When the change ratio is sufficiently small, adsorption performance of the adsorbent tends to be stable. Specifically, the change ratio is preferably within ±5%, more preferably within ±3%, and further preferably within ±2%. Although the measurement method of the dynamic adsorption capacity for the change ratio measurement is not particularly limited, for the purpose of comparison, the dynamic adsorption capacity is measured under the substantially same conditions before and after the test treatment. The details of the measurement method of the change ratio will be described in the examples described below.

The dynamic adsorption capacity of bovine serum albumin or lysozyme after the above-described test treatment of the protein adsorbent according to the present embodiment is, for example, 5 mg/mL or more. Since a protein adsorbent that adsorbs more protein is required, the dynamic adsorption capacity is preferably 10 mg/mL or more, and more preferably 20 mg/mL or more.

The polymer molded body constituting the substrate 3 is a member containing a polymer compound and having a predetermined shape, and for example, can be obtained by shaping a material containing a polymer compound into a predetermined shape. For example, the substrate 3 may be the polymer molded body itself, or may be constituted of the polymer molded body and a coating film formed on the surface of the polymer molded body, which is described below (FIG. 1 is a schematic diagram in the case where the substrate 3 is the polymer molded body itself, and a coating film formed on the surface of the polymer molded body is not shown in the drawing.). Generally, the substrate 3 has the same shape as the polymer molded body. The polymer molded body may be a porous body having the form of a flat membrane, nonwoven fabric, hollow fiber membrane, monolith or bead. The porous body is preferable because it can increase an adsorption surface area. From the viewpoint of ease of handling and capable of achieving a high purifying treatment speed, the membranous form such as flat and hollow fibrous form is more preferable. From the viewpoint of a scale-up property and simpleness of a flow path structure in shaping a module, a hollow fiber porous membrane is particularly preferable. In the present embodiment, the "hollow fiber porous membrane" means a cylindrical or fibrous porous body in which a hollow part is formed by the inner wall. The hollow side (inner side) and the outer side of the hollow fiber porous membrane are continuous through a pore that is a though-hole. The hollow fiber porous membrane has a property in that a liquid or gas permeates from the inner side to the outer side or from the outer side to the inner side through the pore. The outer diameter and the inner diameter of the hollow fiber porous membrane are not particularly limited as long as the porous membrane can physically retains the shape. Alternatively, the polymer molded body may be a non-porous body as long as it has a form capable of bringing a protein solution into contact with its surface. Examples of the non-porous body include a film, a non-porous bead, a fiber, and a capillary.

In the case where the polymer molded body is a membranous porous body, its pore diameter is preferably 0.01 μm to 10 μm, more preferably 0.05 μm to 7 μm, and further preferably 0.1 μm to 1 μm. Although the porosity that is the volume ratio of the pore in the porous body is not particularly limited as long as the shape of the porous body is retained and pressure loss when feeding a liquid is within a practically acceptable range, it is preferably 5% to 99%, more preferably 10% to 95%, and further preferably 30 to 90%. The measurement of the pore diameter and the porosity can be carried out by a conventional method for those skilled in the art, which is described in, for example, "Basic Principles of Membrane Technology" written by Marcel Mulder (Industrial Publishing & Consulting, Inc.). Specific examples thereof include observation by an electron microscope, a bubble point method, a mercury intrusion method, and a transmittance method.

Although the polymer compound forming the polymer molded body constituting the substrate 3 is not particularly limited, for retaining mechanical properties, polyolefin polymers, polysulfone, polyethersulfone, cellulose, and cellulose derivatives are preferable. For example, the polyolefin polymers are selected from homopolymers of olefins such as ethylene, propylene, butylene, and vinylidene fluoride, copolymers of two or more kinds of the olefins, and copolymers of one kind or two or more kinds of olefins and perhalogenated olefins. Among these polymers, because of particularly excellent mechanical strength, polyethylene, polyvinylidene fluoride, and polysulfone are preferable, and in the case where a radiation graft polymerization method is used for forming the molecular chain 5, polyethylene is more preferable.

The adsorption layer 6 formed of the molecular chain 5 containing the weak electrolytic ion-exchange group exists on at least a part of the surface of the substrate 3. The form of the adsorption layer 6 formed of the molecular chain 5 is not particularly limited as long as there are no problems such as dissolution of the adsorption layer 6 and pressure increase when feeding a liquid in a heating step or a protein adsorption/desorption step. The molecular chain 5 is fixed to the substrate 3 by, for example, a covalent bond, covering, or adsorption. The molecular chain 5 is preferably a graft chain covalently-bonded to the polymer compound forming the polymer molded body or a compound forming the coating film formed on the surface of the polymer molded body, which is described below.

The state of the adsorption layer 6 formed of the molecular chain 5 is not limited. For example, the molecular chain 5 may be a linear molecular chain, or may be a polymer chain having a cross-linked structure. In the case of the molecular chain having a cross-linked structure, the adsorption layer 6 may be a gel adsorption layer in which molecular chains are loosely cross-linked to each other on the surface of the substrate, or may be a skin adsorption layer in which molecular chains are strongly cross-linked to each other.

The molecular chain 5 has the weak electrolytic ion-exchange group as a constitutional unit constituting its side chain group, terminal group, or main chain. The weak electrolytic ion-exchange group in the molecular chain 5 can be, for example, a weak electrolytic cation-exchange group or a weak electrolytic anion-exchange group. Examples of the weak electrolytic cation group include a carboxylic acid group ($—COO^-$), phosphate groups ($—PO_3^-$, $—PO_3^{2-}$), and a phosphoester group ($—PO_3R^-$). The weak electrolytic anion-exchange group may be, for example, a primary amino group ($—NH_2$), a secondary amino group ($—NRH$), or a tertiary amino group ($—NR_2$). R is not particularly limited in these ion-exchange groups, and in particular, in the case of the tertiary amino groups, Rs bonded to the same N may be the same or different. Preferably, R represents hydrocarbon groups such as alkyl groups, aryl groups and aralkyl groups. For example, the tertiary amino group may be introduced into the molecular chain (graft chain) as a diethylaminoethyl group (DEAF, $—(CH_2)_2—NEt_2$) or a diethylaminopropyl group (DEAF, $—(CH_2)_3—NEt_2$).

The substrate 3 may further comprise a coating film that covers at least a part of the surface of the polymer molded body with a different material or the polymer compound having a different microstructure from the polymer molded body. In this case, a part or all of a plurality of molecular chains 5 may be fixed on the surface of the coating film. The coating film may be formed by coating with a polymer compound such as nylon through aggregation or adsorption, may be formed as network coating with a reactive coating material such as a urethane resin, or may be formed by a covalent bond on the surface of the polymer molded body. In order to prevent detachment of covering from the adsorbent, covering is preferably formed by network coating or a covalent bond with respect to the polymer molded body.

The adsorbent 1 according to the present embodiment can be produced by, for example, a method comprising a step of obtaining a pretreatment adsorbent comprising the substrate 3 comprising the polymer molded body and the molecular chain 5 fixed on the surface of the substrate 3, in which the molecular chain 5 contains the weak electrolytic ion-exchange group (molecular chain forming step), a step of heating the pretreatment adsorbent (dry-heat treatment step), and a step of heating the pretreatment adsorbent after moistening the pretreatment adsorbent with a liquid or steam (wet-heat treatment step), in this order.

A method of introducing the molecular chain 5 on the surface of the substrate 3 is not particularly limited. There are a method in which radicals are generated by irradiation to the polymer molded body to form a graft chain as the molecular chain 5 by graft polymerization from the polymer compound forming the polymer molded body, a method in which the polymer compound having the weak electrolytic ion-exchange group is attached to the substrate, and then, the polymer compound as the molecular chain 5 is fixed on the surface of the substrate by a cross-linking agent, a method in which a coating film of a polymer or a polymer precursor, which covers the surface of the polymer molded body, is formed to obtain the substrate 3, and then, a graft chain is made to be formed as the molecular chain 5 from the polymer compound constituting the coating film, and the like. In particular, in the case where a strong bond by a covalent bond between the polymer molded body or the polymer compound that forms the coating film covering its surface and the molecular chain 5 is expected, a method of introducing the molecular chain 5 by graft polymerization from the polymer molded body or the polymer compound that forms the coating film is preferable.

In the case where the molecular chain 5 is introduced by graft polymerization from the polymer molded body or the polymer compound that forms the coating film, (1) a method in which a monomer having the weak electrolytic ion-exchange group is directly polymerized, or (2) a method in which a graft chain containing a reactive functional group is introduced by graft polymerization from the polymer compound, and then, the weak electrolytic ion-exchange group is introduced into the graft chain by the reaction of the reactive functional group, can be adopted.

The method (1) is simple because the molecular chain 5 can be introduced by one-step reaction. Although the monomer is not particularly limited, examples thereof include methacrylate derivatives, vinyl compounds, and allyl compounds. For example, the monomer can be selected from diethylaminoethyl methacrylate, allylamine, acrylic acid, and methacrylic acid.

The method (2) has an advantage in the wide range of choice in the kind of the weak electrolytic ion-exchange group and the introduction ratio of the weak electrolytic ion-exchange group. As the monomer to be graft polymerized by this method, glycidyl methacrylate (GMA) having a highly-reactive epoxy group is preferable. That is, the molecular chain 5 is preferably a polymer chain derived from a polyglycidyl methacrylate chain.

The amount of the molecular chain 5 and the amount of the weak electrolytic ion-exchange group to be introduced into the molecular chain 5 are not particularly limited as long as there are no problems such as pressure increase when feeding a liquid. The amount of the molecular chain 5 and the weak electrolytic ion-exchange group will be described below with reference to the case of the method (2) by graft polymerization.

In general, the binding ratio of the graft chain with respect to the substrate (graft ratio, dg [%]) is defined based on the mass increased by the introduction of the graft chain, as represented by the following expression (1).

[Expression 1]

$$dg[\%] = \frac{W_1 - W_0'}{W_0} \times 100 \quad (1)$$

$W_0$: mass of polymer molded body before reaction (g)
$W_0'$: mass of substrate before introducing graft chain (g)
$W_1$: total mass after introducing graft chain (g)

In the expression (1), when the substrate is constituted of the polymer molded body itself, $W_0'=W_0$.

The existence ratio of the weak electrolytic ion-exchange group with respect to the reactive functional group (functional group capable of introducing weak electrolytic ion-exchange group) in the graft chain is organized by the "ligand inversion ratio" represented by the expression (2). That is, the existence ratio of the weak electrolytic ion-exchange group is represented by the molar number of the weak electrolytic ion-exchange group introduced into the graft chain with respect to the molar number of the reactive functional group in the graft chain. For example, in the case where the graft chain is the polymer of GMA and a diethylamino group is introduced by the reaction of the epoxy group of GMA and diethylamine, the molecular weight of GMA 142 g/mol and the molecular weight of diethylamine 73 g/mol are respectively substituted into $M_1$ and $M_2$ in the expression (2).

[Expression 2]

$$T[\%] = \frac{(W_2 - W_1)/M_2}{(W_1 - W_0')/M_1} \times 100 \quad (2)$$

$W_0'$: mass of substrate before introducing graft chain (g)
$W_1$: total mass after introducing graft chain (g)
$W_2$: total mass after introducing weak electrolytic ion-exchange group (g)
$M_1$: molecular weight of monomer unit forming graft chain (g/mol)
$M_2$: molecular weight of weak electrolytic ion-exchange group (g/mol)

From the viewpoint of securing both of higher adsorption capacity and dynamically-stable strength, the graft ratio is preferably 5% to 200%, more preferably 20% to 150%, and further preferably 30% to 90%. From the viewpoint of obtaining higher adsorption capacity, the ligand inversion ratio is preferably 20% to 100%, more preferably 50% to 100%, and further preferably 70% to 100%.

In the case of the method according to the present embodiment, the dry-heat treatment is performed by heating the pretreatment adsorbent in a dry state, in other words, in the state where at least a part of it is not moistened with a liquid or steam. The dry-heat treatment may be performed with respect to the pretreatment adsorbent itself, or may be performed in the form in which the pretreatment adsorbent is packed in a housing (for example, module, column and the like). In both cases, the substantially similar effect is exhibited.

The pretreatment adsorbent into which the molecular chain 5 is introduced can be obtained in the state where, for example, a reaction solvent for introducing the molecular chain 5 by a liquid phase reaction or a liquid used for washing or the like after the reaction (for example, moisture) adheres to the substrate. Alternatively, the molecular chain 5 is introduced by a gas phase reaction and the pretreatment adsorbent is sometimes obtained in the state where a liquid does not substantially adhere to the substrate. The pretreatment adsorbent produced by the liquid phase reaction can be kept in the state where at least a part of the pretreatment adsorbent is not moistened with a liquid or steam by performing drying treatment for removing in advance a liquid that adheres to the substrate, before performing the dry-heat treatment. Alternatively, a front half part of successive heating steps is used as drying treatment for keeping the state where at least a part is not moistened with a liquid or steam, and a subsequent latter half part can be used as the dry-heat treatment according to the present embodiment. The heating temperature and the heating time for the dry-heat treatment are adjusted such that the change ratio of the dynamic adsorption capacity of the adsorbent before and after the above-described test treatment is small and the stabilization effect of adsorption performance is sufficiently obtained. Moreover, the heating temperature and time are equal to or more than temperature and time by which the pretreatment adsorbent is sufficiently dried, and are adjusted to equal to or less than temperature and time by which strength deterioration and melting do not occur. Furthermore, in the case of performing a step of incorporating the pretreatment adsorbent into a housing (for example, module, column and the like), they are adjusted to temperature and time by which complete hardening of a sealing material for bonding the housing to the pretreatment adsorbent is achieved. Specifically, the heating temperature is preferably 40 to 130° C., more preferably 45° C. to 110° C., and further preferably 50 to 95° C. The heating time is preferably 1 to 150 hours and more, more preferably 2 to 100 hours, and further preferably 4 to 60 hours.

After the dry-heat treatment, the pretreatment adsorbent is moistened with a liquid or steam, and then, the wet-heat treatment for heating the pretreatment adsorbent in the moistened state is performed. By the combination of the dry-heat treatment and the wet-heat treatment, the adsorbent with a small change ratio in the above-described test treatment can be efficiently produced. Although the mechanism that exhibits this effect is not necessarily clear, it is considered that this is because, by combining the dry-heat treatment and the wet-heat treatment in this order, molecular chains are efficiently rearranged and the form of the molecular chains becomes stable. For example, it is considered that the polymer structure of the substrate itself is loosened in the dry-heat treatment and the molecular chain structure constrained in the vicinity of the surface of the substrate is released, or the molecular chains pass through a state where they shrink during the dry-heat treatment, and the molecular chains are thereby efficiently rearranged when the molecular chains extend again by the subsequent wet-heat treatment so that the form of the molecular chains becomes stable.

In the present embodiment, the "moistened state" refers to a state where the surface of the pretreatment adsorbent (for example, pore surface) is moistened with a liquid (wet-heat treatment liquid). In the case where the pretreatment adsorbent in a dry state is moistened, the adsorbent may be moistened by once performing hydrophilization treatment, and then finally being substituted with a wet-heat treatment liquid. The hydrophilization treatment can be performed by a method of bringing, for example, water, an alcohol aqueous solution, an alcohol, or steam into contact with the pretreatment adsorbent. The hydrophilization may be accelerated by pressurizing and/or heating. Among them, the hydrophilization treatment with an alcohol or an alcohol aqueous solution can be performed by various materials and forms. Moreover, the pretreatment adsorbent is moistened with an alcohol or an alcohol aqueous solution, the alcohol or the alcohol aqueous solution is once substituted with pure water, and then, the pretreatment adsorbent may be finally in the moistened state with a wet-heat treatment liquid. As one example of moistening, there is a method in which the pretreatment adsorbent is brought into contact with ethanol or an ethanol aqueous solution, the ethanol or the ethanol aqueous solution is once substituted with pure water by gradually increasing the ratio of the pure water, and is finally substituted with a wet-heat treatment liquid. The method of substitution with a wet treatment liquid is not limited as long as the pretreatment adsorbent is sufficiently substituted with the wet treatment liquid. For example, in the case where the pretreatment adsorbent is membranous, a method of feeding a wet treatment liquid is effective so as to sufficiently perform hydrophilization or substitution of a solution.

In the present description, the "moistened state" of the adsorbent means that, more specifically, the degree of moistening is 0.1 or more, for example. The measurement of the degree of moistening can be performed in accordance with the following procedure.

1. In the case of an adsorbent in a column or a module, it is disassembled and a certain amount of the adsorbent is taken out.

2. After a surplus filling preservative solution that adheres to the adsorbent is removed, the liquid-containing mass $W_W$ of the adsorbent is measured.

3. After the adsorbent to which the filling preservative solution adheres is sufficiently washed with ethanol and water, it is dried in an oven at 65° C. for 16 hours, and the dry mass $W_D$ of the adsorbent is measured.

4. The degree of moistening is calculated from the liquid-containing mass $W_W$ and the dry mass $W_D$ of the adsorbent, based on the following expression.

$$\text{wettability}=(W_W-W_D)/W_D$$

The heating temperature and the heating time in the wet-heat treatment are adjusted such that the change ratio of the dynamic adsorption capacity of the adsorbent before and after the above-described test treatment is small and the stabilization effect of adsorption performance is sufficiently obtained. Specifically, the heating temperature is preferably 40 to 130° C. or 40 to 120° C. In order to perform heating reliably, 50 to 130° C. or 50 to 120° C. is more preferable. For example, considering ease or economic efficiency of treatment equipment maintenance, a wet treatment liquid is used while making it to be water, and 50 to 99° C. is more preferable, and the wet-heat treatment is further preferably performed at 70 to 99. Furthermore, in the case of performing the wet-heat treatment involving sterilization, 100 to 130° C. is more preferable, and 120 to 130° C. is further more preferable. The heating time is preferably 30 minutes or more, more preferably 1 hour or more, and further preferably 3 hours or more so as to perform heating reliably.

The method of heating the pretreatment adsorbent is not particularly limited as long as the pretreatment adsorbent in the moistened state is sufficiently heated and mechanical strength of the adsorbent is not affected. The wet-heat treatment may be performed with respect to the pretreatment adsorbent itself, or may be performed in the form in which the pretreatment adsorbent is packed in a housing (for example, module, column and the like), and in both cases, the substantially similar effect is exhibited. The wet-heat treatment of the pretreatment adsorbent can be performed through a heating method like heating by a hot-water bath, heating by steam contact under high pressure by an autoclave, feeding a heated wet treatment liquid or feeding steam of a wet treatment liquid. When heating from the outside of the housing or when heating by an autoclave, the amount of the solution enclosed in the housing is not limited, and the wet-heat treatment liquid may be in a completely dripped state or in a filled state.

The wet-heat treatment liquid for moistening the pretreatment adsorbent is preferably pure water or an aqueous solution. When the heating temperature is 110° C. or less, examples thereof include pure water, a buffer solution, an inorganic salt aqueous solution, and a buffer solution containing an inorganic salt. In general, when a protein is adsorbed to the adsorbent, a buffer solution in which a protein is dissolved is used, and when a protein is desorbed, a buffer solution containing sodium chloride is used. Therefore, it is convenient to use a buffer solution as the wet-heat treatment liquid. When the heating temperature exceeds 110° C. and is 130° C. or less, the treatment liquid is preferably an aqueous solution containing an inorganic salt. In this case, a cationic species, an anionic species, and a valence are not limited. Examples of a monovalent cation include a lithium ion, a sodium ion, and a potassium ion, and examples of a divalent cation include a magnesium ion and a calcium ion. Examples of the anionic species include a hydroxide ion, a chloride ion, a bromide ion, a sulfate ion, and a nitrate ion, and the combination with a cation is not limited. Since the wet-heat treatment liquid is generally used as a protein eluate or a wash solution, a buffer solution containing an inorganic salt or a sodium hydroxide aqueous solution is preferable, and a buffer solution containing sodium chloride is more preferable. The concentration of the metal ion is preferably 0.05 mol/L or more, more preferably 0.1 mol/L or more, and further preferably 1 mol/L or more.

It is considered that the dry-heat treatment and the subsequent wet-heat treatment according to the present embodiment accelerates rearrangement of the molecular chains covering the substrate and stabilizes adsorption performance. The pretreatment adsorbent to be effectively rearranged preferably has linear graft polymer chains directly formed from the substrate, or polymer chains that loosely cross-links to each other to form a gel coating film. The pretreatment adsorbent having linear graft polymer chains directly formed from the substrate is more preferable. When the wet-heat treatment is performed with respect to these pretreatment adsorbents, an effect of stabilizing adsorption performance can be particularly significantly obtained.

The pretreatment adsorbent subjected to the dry-heat treatment and the wet-heat treatment is not necessarily an unused adsorbent (adsorbent that has never adsorbed protein). For example, an adsorbent whose adsorption capacity is decreased by repeating adsorption and desorption, or an adsorbent whose adsorption capacity is decreased by heat treatment different from the present embodiment is used as the pretreatment adsorbent, and the wet-heat treatment may be performed with respect to this.

After the wet-heat treatment, the obtained adsorbent can be maintained in the moistened state. The moistened state of the adsorbent is maintained, for example, between after the wet-heat treatment and until it is used for protein adsorption. The degree of moistening of the adsorbent after the wet-heat treatment may be maintained to be 0.1 or more, or maintained to be 0.5 or more or 1.0 or more. Although the upper limit of the degree of moistening is not particularly limited, for example, the degree of moistening may be 3.0 or less.

In order to maintain the moistened state of the adsorbent, after the wet-heat treatment of the adsorbent in the module or the column, the wet-heat treatment liquid may be substituted with a filling preservative solution such as water, an alcohol, or an alcohol aqueous solution, or the adsorbent may remain moistened with the wet-heat treatment liquid. When it is difficult to maintain the moistened state due to volatilization of moisture in the filling preservative solution during storage, a filling preservative solution containing a moisturizing agent such as glycerin may be used. Moreover, in the case where a sterilization or bacteriostatic effect is expected, an ethanol aqueous solution can be used as the filling preservative solution.

In order to maintain the moistened state of the adsorbent, the module or the column may be filled with the filling preservative solution, or may be in a so-called completely dripped state by eliminating a surplus filling preservative solution.

The adsorbent according to the present embodiment can be used for protein separation and purification and the like, for example, in the form of a column or a module. The module is composed of, for example, a membranous adsorbent and a housing that houses the adsorbent. In particular, in the case where the adsorbent is a hollow fiber membrane, the module may comprise a housing having openings at both ends, and one or a plurality of hollow fiber membranes fixed in the housing. A liquid in which a protein is dissolved, which is supplied from a nozzle at the housing opening side, passes through the membrane from the inner side to the outer side of the hollow fiber, and is discharged from a nozzle attached to the side surface of the housing. The column is composed of, for example, a particulate adsorbent and a tubular container that houses the adsorbent.

EXAMPLES

Hereinafter, the present invention will be described more specifically with reference to examples. However, the present invention is not limited to these examples.

In the following examples and comparative examples, the measurement of the dynamic adsorption capacity and the change ratio of the dynamic adsorption capacity before and after the test treatment was performed in accordance with the following procedure.

(Measurement Method of Dynamic Adsorption Capacity)

As an index protein solution for measuring the dynamic adsorption capacity, both of BSA (bovine serum albumin, manufactured by Sigma-Aldrich Co. LLC.) for an adsorbent containing a weak electrolytic anion-exchange group (diethylamino group) and lysozyme (manufactured by Sigma-Aldrich Co. LLC.) for an adsorbent containing a weak electrolytic cation-exchange group (carboxylic acid group) are prepared by the following procedure. BSA or lysozyme is dissolved at the concentration of 1 g/L in a 20 mM tris-hydrochloric acid buffer solution that is adjusted to pH 8 (hereinafter, referred to as "buffer solution"). The obtained index protein solution (BSA solution or lysozyme solution) is made to pass through a 0.45 μm filter.

A module is connected to a HPLC system (GE Healthcare Japan AKTAexplorer 100). The buffer solution (50 MV), the index protein solution (67 MV), the buffer solution (17 MV), and the buffer solution containing 1 mol/L sodium chloride (salt buffer solution) (25 MV) are sequentially fed at the liquid sending speed of 5 MV/min. The "MV" means a membrane volume, and "1 MV" corresponds to feeding a liquid of the same amount as the membrane volume. The calculation method of the membrane volume will be described below. The first feeding of the buffer solution is performed for the purpose of equilibration of the membrane, and the second feeding of the buffer solution after supplying the index protein solution is performed for the purpose of washing of the non-adsorbed index protein. Furthermore, feeding of the salt buffer solution after that is performed for the purpose of elution of the adsorbed index protein.

The liquid feeding speed can be arbitrarily set to the extent that the adsorbent and its module can maintain the shapes and can maintain the adsorbing function. The amount of each feeding liquid can be arbitrarily set in accordance with a size of the module to be evaluated as long as it sufficiently substitutes the liquid that is previously fed (for example, in the case of the first feeding of the buffer solution, the enclosed liquid that moistens the adsorbent) and is the amount to achieve the purpose of the liquid (for example, equilibration, washing). The amount of the feeding liquid can be confirmed to be sufficient when pH, conductivity, and absorbance of each liquid after being fed through the adsorbent are monitored and the liquid is in an equilibrium state.

While feeding the index protein solution, absorbance of filtrate discharged from the module at a wavelength of 280 nm is measured, and the amount of the filtrate when the ratio of the absorbance of the filtrate to absorbance of a raw solution (index protein solution before being fed) becomes 10% is confirmed. The amount of the filtrate is converted into the mass of the index protein based on the concentration of 1 g/L, and the amount of adsorption of the index protein [mg] when the absorbance ratio becomes 10% is calculated. Furthermore, the calculated value is divided by the membrane volume (in the case of hollow fiber, inner and outer diameter of hollow fiber, volume of circular part calculated from effective fiber length) to determine the adsorption capacity (mg/mL) of the index protein (BSA or lysozyme) per the membrane volume. This value is called the "dynamic adsorption capacity", and is generally used in the field of biotechnology.

(Change Ratio Before and after Test Treatment)

The module in which the dynamic adsorption capacity is measured by the above-described method in advance and which is filled with the salt buffer solution (20 mM tris-hydrochloric acid buffer solution containing 1 mol/L sodium chloride, pH 8) is prepared. If the index protein is adsorbed to the adsorbent, the index protein is made to be eluted by feeding the salt buffer solution through the module. If the module is not filled with the salt buffer solution, the salt buffer solution is sufficiently fed, and conductivity of the salt buffer solution after the feeding is confirmed to be 65 mS/cm or more (CONDUCTIVITY METER B-173 manufactured by HORIBA, Ltd.). The module whose liquid flow path is sealed is put in a water bath set to 50° C. in advance, and heating is continued at 50° C. for 8 hours (test treatment). The dynamic adsorption capacity of the module after the test treatment is measured by the above-described method. A degree of change of the dynamic adsorption capacity after the test treatment with respect to the dynamic adsorption capacity before the test treatment is determined as the change ratio before and after the test treatment (%), based on the following expression.

Change ratio before and after test treatment=(dynamic adsorption capacity after test treatment/dynamic adsorption capacity before test treatment)×100−100

Example 1

Production of Adsorbent

Hollow Fiber Porous Membrane Having Graft Chain 27.2 parts by mass of silicate fine powder (AEROSIL R972 grade), 54.3 parts by mass of dibutyl phthalate (DBP), and 18.5 parts by mass of polyethylene resin powder (Asahi Kasei SUNFINE SH-800 grade) were preliminary mixed, and was extruded to be hollow fiber by a twin-screw extruder to obtain a hollow fiber membrane. Next, the membrane was sequentially soaked in methylene chloride and a sodium hydroxide aqueous solution to extract dibutyl phthalate (DBP) and silicate, and then, was subjected to washing with water and drying treatment to obtain a hollow fiber porous membrane that is a polyethylene molded body.

The obtained hollow fiber porous membrane was put in an airtight container, and the inside of the container was substituted with nitrogen gas. Then, the airtight container having therein the hollow fiber porous membrane was put in a box made of Styrofoam with dry ice, and was irradiated with γ ray of 200 kGy while being cooled to generate radicals on polyethylene and activate the hollow fiber porous membrane.

The activated hollow fiber porous membrane was returned to room temperature in the airtight container under a nitrogen atmosphere. Then, the hollow fiber porous membrane was put in a reaction container, and the reaction container is air-tightly sealed to be in a vacuum state (100 Pa or less). A reaction solution prepared in advance by mixing 5 parts by mass of glycidyl methacrylate (GMA) and 95 parts by mass of methanol and bubbling it with nitrogen was sent into the reaction container in the vacuum state using a pressure difference. The sent reaction solution was circulated at 40° C. for 4 hours, and left at rest all night long, and then, the reaction solution was discharged. The hollow fiber porous membrane was sufficiently washed with methanol and water in this order to obtain a graft hollow fiber porous membrane having a graft chain formed by graft polymerization of glycidyl methacrylate on the polyethylene main chain. The graft ratio determined by the above-described expression (1) was 85%.

A diethylamine aqueous solution having a concentration of 50 parts by volume was charged in the reaction container having therein the graft hollow fiber porous membrane, circulated at 30° C. for 5 hours, and left at rest all night long, and then, the diethylamino aqueous solution was discharged. Next, the hollow fiber porous membrane was sufficiently washed with water and dried to obtain a graft hollow fiber porous membrane having a diethylamino (DEA) group (weak electrolytic ion-exchange group) as a ligand bonded to the graft chain, as the adsorbent. The ligand inversion ratio determined by the above-described expression (2) was 95%. Two modules each having one fiber having a fiber effective length of 9.4 cm were assembled using this graft hollow fiber porous membrane.

One module (module A) was directly heated at 90° C. for 6 hours (dry-heat treatment). The dry-heat treatment was performed under atmospheric pressure using a forced-circulation drier as a heating device. After that, the inside of the module was filled with water as a wet-heat treatment liquid, and the module was heated for 20 hours with the adsorbent in a moistened state (wet-heat treatment). The wet-heat treatment was performed under atmospheric pressure using a water bath as a heating device. The dynamic adsorption capacity $A_{00}$ of the module A after the wet-heat treatment was measured. The measurement of the dynamic adsorption capacity was performed using the BSA solution.

Another module (module B) was directly heated at 90° C. for 6 hours (dry-heat treatment). After that, the inside of the module was filled with water as a wet-heat treatment liquid, and the module was heated for 20 hours with the adsorbent in a moistened state (wet-heat treatment). Next, the module was stored for 240 days in an indoor environment at 10 to 30° C. The module B after being stored was subjected to the test treatment, and the dynamic adsorption capacity $A_0$ before the test treatment and the dynamic adsorption capacity $A_1$ after the test treatment were measured.

Furthermore, the above-described module B after the first test treatment was subjected to second test treatment, and the dynamic adsorption capacity $A_2$ after the test treatment was measured.

Example 2

The graft hollow fiber porous membrane having the graft ratio and the ligand inversion ratio shown in Table 1 was produced as the adsorbent by the same method as Example 1. After drying from a wet state with water for washing, the same module as Example 1 was assembled, and, in that state, the dry-heat treatment of the adsorbent was performed by heating at 50° C. for 48 hours under atmospheric pressure using a forced-circulation drier. The adsorbent after the dry-heat treatment was subjected to the wet-heat treatment under conditions shown in Table 1. The wet-heat treatment was performed by a method of circulating hot water in the adsorbent. The dynamic adsorption capacities $A_{00}$, $A_0$ and $A_1$ of the adsorbent after the wet-heat treatment were measured in the same manner as Example 1.

Example 3

The graft hollow fiber porous membrane having the graft ratio and the ligand inversion ratio shown in Table 1 was produced as the adsorbent by the same method as Example 1. The adsorbent was dried by heating for 4 hours subsequently after washing with water, and the dry-heat treatment of the adsorbent was performed by directly heating the dried adsorbent at 70° C. for 12 hours under atmospheric pressure using a forced-circulation drier. After the dry-heat treatment, the same module as Example 1 was assembled, and the adsorbent was subjected to the wet-heat treatment under conditions shown in Table 1. The dynamic adsorption capacities $A_{00}$, $A_0$ and $A_1$ of the adsorbent after the wet-heat treatment were measured in the same manner as Example 1.

Example 4

The graft hollow fiber porous membrane having the graft chain containing a carboxylic acid group (weak electrolytic cation-exchange group) as a ligand was produced by using acrylic acid in place of glycidyl methacrylate and graft polymerizing this. The graft ratio was 35%. The adsorbent was dried by heating at 40° C. from a wet state with water for washing, and the dry-heat treatment of the adsorbent was performed by directly heating the dried adsorbent at 70° C. for 4 hours under atmospheric pressure using a forced-circulation drier. After the dry-heat treatment, the same module as Example 1 was assembled, and the adsorbent was subjected to the wet-heat treatment under conditions shown in Table 1. The dynamic adsorption capacities $A_{00}$, $A_0$ and $A_1$ of the adsorbent after the wet-heat treatment were measured in the same manner as Example 1 except that the lysozyme solution was used as the index protein solution.

Example 5

Nylon 6 (0.2 g), methylene chloride (10 g), and 0.1 g of formic acid were stirred at room temperature, 2 g of t-butyl sodium hypochlorite was added thereto, and dissolution of nylon 6 was waited. Methylene chloride was further added to the obtained solution such that the total mass is 100 g to obtain a N-chloro-nylon 6 solution for forming a coating film.

A porous flat membrane (Nihon Millipore K.K.) made of a cellulose derivative having a pore diameter of 0.45 μm and a membrane thickness of 0.15 mm was soaked in the N-chloro-nylon 6 solution, and impregnation of a porous part with the solution was waited. A surplus solution was removed from the porous flat membrane that was impregnated with the solution, the membrane was firstly dried at room temperature, and then, further dried in a hot-air circulation drier at 80° C., and finally heated at 140° C. for 15 minutes to obtain a flat membrane substrate having the cellulose derivative and a N-chloro-nylon 6 coating film that covers its surface.

A sodium phosphate buffer solution (pH 7.5) having a composition of 5% of glycidyl methacrylate (GMA), 0.3% of Tween 80 (manufactured by Kanto Chemical Co., Inc.) and 0.1% of sodium dithionite was well stirred in a reaction container. The above-described flat membrane substrate was put in the sodium phosphate buffer solution, and a graft polymerization reaction was performed at room temperature for 12 minutes. The membrane after the reaction was washed with pure water and acetone in this order, and dried at 80° C. to obtain a graft porous flat membrane having a graft chain formed by graft polymerization of GMA. The graft ratio determined by the above-described expression (1) was 8%.

The graft porous flat membrane was subjected to the same reaction as Example 1 to obtain a porous flat membrane having a diethylamino (DEA) group (weak electrolytic ion-exchange group) as a ligand bonded to the graft chain, as the adsorbent. The ligand inversion ratio determined by the above-described expression (2) was 96%.

Two modules each having a total membrane thickness of 8 mm and an effective membrane area of 15 cm$^2$ were assembled by stacking the five obtained graft porous flat membranes and sandwiching it with a stainless filter holder in that state. After that, the adsorbent was subjected to the dry-heat treatment and the wet-heat treatment under conditions shown in Table 1. The dynamic adsorption capacities $A_{00}$, $A_0$ and $A_1$ of the adsorbent after the wet-heat treatment were measured in the same manner as Example 1.

Comparative Example 1

The module was produced in the same manner as Example 1 except that the wet-heat treatment was not performed, and the dynamic adsorption capacities $A_{00}$, $A_0$ and $A_1$ thereof were measured.

Comparative Example 2

The module was produced in the same manner as Example 1 except that the dry-heat treatment was not performed, and the dynamic adsorption capacities $A_{00}$, $A_0$ and $A_1$ thereof were measured.

Examples 6 to 11

The graft hollow fiber porous membrane having the graft ratio and the ligand inversion ratio shown in Table 2 was produced as the adsorbent by the same method as Example 1. The same module as Example 1 was assembled using each adsorbent. The adsorption capacities $A_0$ and $A_1$ of the adsorbent were measured in the same manner as Example 1 except that the obtained module was subjected to the dry-heat treatment and the wet-heat treatment under conditions shown in Table 2. The wet-heat treatment of Example 8 was performed by a method of circulating hot water in the adsorbent in place of heating by a water bath. The wet-heat treatment of Example 10 was performed by a method of heating the module in a state of being soaked in a hot-water bath at 90° C., for 6 hours in a drier at 90° C. in place of heating by a water bath. The wet-heat treatment of Example 13 was performed in an autoclave set to 121° C. by a method of making a surplus liquid completely dripped from a wet state with the salt buffer solution as a wet-heat treatment liquid in the module, and heating the module while pressurizing the module in a state where all nozzles of a housing are opened.

The measurement results are shown in Table 1 and Table 2. Regarding any module of Examples 1 to 13, the change ratio of the dynamic adsorption capacity before and after the test treatment (change ratio of $A_1$ to $A_0$) was within ±5%. The change ratios of the modules of Comparative Examples 1 and 2 before and after the test treatment reached about 10% to 20%.

TABLE 1

|  |  | Example 1 | Example 2 | Example 3 | Example 4 | Example 5 | Comparative Example 1 | Comparative Example 2 |
|---|---|---|---|---|---|---|---|---|
| graft chain | kind | GMA | GMA | GMA | acrylic acid | GMA | GMA | GMA |
|  | graft ratio | 85 | 55 | 185 | 35 | 8 | 63 | 57 |
| ligand | kind | DEA | DEA | DEA | carboxylic acid | DEA | DEA | DEA |
|  | inversion ratio | 95 | 98 | 75 | 100 | 96 | 93 | 96 |
| dry-heat treatment | form | module | module | membrane | membrane | module | module | nothing |
|  | temperature | 90° C. | 50° C. | 70° C. | 70° C. | 90° C. | 90° C. |  |
|  | time | 6 hr | 48 hr | 12 hr | 4 hr | 6 hr | 6 hr |  |
| wet-heat treatment | temperature | 50° C. | 90° C. | 70° C. | 50° C. | 50° C. | nothing | 50° C. |
|  | time | 20 hr | 2.5 hr | 8 hr | 8 hr | 20 hr |  | 20 hr |
|  | treatment liquid | water | water | buffer solution | buffer solution | water |  | water |
|  | heating method | water bath | filtration circulation of hot water | water bath | water bath | water bath |  | water bath |
| dynamic adsorption capacity $A_{00}$ |  | 67.9 | 55.6 | 71.9 | 52.6 | 69.4 | 61.4 | 68.7 |
| dynamic adsorption capacity $A_0$ |  | 68.7 | 55.8 | 70.4 | 53.4 | 66.1 | 54.5 | 62.2 |
| change ratio with respect to $A_{00}$ |  | 1.2% | 0.4% | −2.1% | 1.5% | −4.8% | −11.2% | −9.5% |
| dynamic adsorption capacity $A_1$ |  | 69.1 | 55.4 | 71.9 | 53.1 | 63.6 | 65.6 | 69.7 |
| change ratio with respect to $A_0$ |  | 0.6% | −0.7% | 2.1% | −0.6% | −3.8% | 20.4% | 12.1% |
| dynamic adsorption capacity $A_2$ |  | 69.0 |  |  |  |  |  |  |
| change ratio with respect to $A_0$ |  | 0.4% |  |  |  |  |  |  |

TABLE 2

|  |  | Example 6 | Example 7 | Example 8 | Example 9 | Example 10 | Example 11 | Example 12 | Example 13 |
|---|---|---|---|---|---|---|---|---|---|
| graft chain | kind | GMA | GMA | GMA | GMA | GMA | GMA | GMA | GMA |
|  | graft ratio | 60 | 69 | 64 | 75 | 63 | 71 | 59 | 68 |
| ligand | kind | DEA | DEA | DEA | DEA | DEA | DEA | DEA | DEA |
|  | inversion ratio | 97 | 96 | 90 | 85 | 95 | 97 | 98 | 97 |
| dry-heat treatment | form | module | module | module | module | module | module | module | module |
|  | temperature | 90° C. | 90° C. | 90° C. | 90° C. | 90° C. | 90° C. | 90° C. | 90° C. |
|  | time | 6 hr | 6 hr | 6 hr | 6 hr | 6 hr | 6 hr | 6 hr | 6 hr |
| wet-heat treatment | temperature | 42° C. | 63° C. | 90° C. | 80° C. | 90° C. | 90° C. | 74° C. | 121° C. |
|  | time | 8 hr | 20 hr | 4 hr | 9.5 hr | 6 hr | 9.5 hr | 20 hr | 1 hr |
|  | treatment liquid | buffer solution | 20% EtOH solution | water | salt buffer solution | buffer solution | buffer solution | buffer solution | salt buffer solution |
|  | heating method | water bath | water bath | filtration circulation of hot water | water bath | hot-water bath in drier | water bath | water bath | autoclave |
| dynamic adsorption capacity $A_0$ |  | 63.0 | 68.6 | 65.2 | 62.9 | 64.4 | 70.4 | 62.6 | 65.1 |
| dynamic adsorption capacity $A_1$ |  | 63.2 | 67.6 | 64.9 | 62.3 | 64.4 | 70.6 | 62.9 | 63.9 |
| change ratio with respect to $A_0$ |  | 0.3% | −1.5% | −0.5% | −1.0% | 0.0% | 0.3% | 0.5% | −1.8% |

Regarding the modules of Examples 1 to 5, there is little difference between the dynamic adsorption capacities $A_{00}$ and $A_0$, and it was confirmed that stability when storing for a long time is excellent. In contrast, in the case of Comparative Examples 1 and 2 having a large change ratio by the test treatment, the dynamic adsorption capacity $A_{00}$ was significantly decreased compared to the dynamic adsorption capacity $A_0$, and stability when storing for a long time was poor. From this result, it was confirmed that the module with little change in the dynamic adsorption capacity before and after the test treatment can exhibit excellent long storage stability.

Furthermore, the module of Example 1 maintained high adsorption performance after performing the second test treatment. Accordingly, it was confirmed that the adsorbent even after protein adsorption and desorption exhibits high stability.

REFERENCE SIGNS LIST

1: adsorbent (hollow fiber porous membrane), 3: substrate, 5: graft chain, 6: adsorption layer, 7: pore, 10: protein

The invention claimed is:

1. A method for producing a protein adsorbent comprising a substrate and a molecular chain fixed to a surface of the substrate, the method comprising, in this order:
   a dry-heat treatment step of heating a pretreatment adsorbent comprising the substrate and the molecular chain fixed on the surface of the substrate, the molecular chain comprising a weak electrolytic ion-exchange group; and
   a wet-heat treatment step of heating the dry-heated adsorbent in a moistened state with a liquid selected from pure water, a buffer solution, an inorganic salt aqueous solution, and a buffer solution comprising an inorganic salt, or steam thereof, and
   wherein the moistened state of the protein adsorbent is maintained after the wet-heat treatment step to obtain the protein adsorbent.

2. The method according to claim 1, further comprising a molecular chain forming step of fixing the molecular chain on the surface of the substrate before the dry-heat treatment step.

3. The method according to claim 1, wherein a dynamic adsorption capacity of bovine serum albumin or lysozyme of the protein adsorbent is 5 mg/mL or more.

4. The method according to claim 1, wherein the dry-heat treatment step comprises heating the pretreatment adsorbent at 40° C. to 130° C. for 1 hour or more.

5. The method according to claim 1, wherein the wet-heat treatment step comprises heating the pretreatment adsorbent at 40 to 120° C. for 30 minutes or more in the moistened state.

* * * * *